(12) United States Patent
St. Germain

(10) Patent No.: US 6,997,945 B2
(45) Date of Patent: Feb. 14, 2006

(54) VARIABLE EXPANSION FORCE STENT

(75) Inventor: Jon P. St. Germain, Elk River, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 509 days.

(21) Appl. No.: 10/106,162

(22) Filed: Mar. 26, 2002

(65) Prior Publication Data

US 2002/0099406 A1   Jul. 25, 2002

Related U.S. Application Data

(63) Continuation of application No. 09/606,898, filed on Jun. 29, 2000, now Pat. No. 6,423,084, which is a continuation of application No. 09/193,504, filed on Nov. 17, 1998, now Pat. No. 6,146,403, which is a continuation of application No. 08/861,798, filed on May 22, 1997, now Pat. No. 5,836,966.

(51) Int. Cl.
A61F 2/06 (2006.01)

(52) U.S. Cl. ...................... 623/1.15; 623/1.2

(58) Field of Classification Search ............. 606/198, 606/194, 195, 191, 192; 623/1.11, 1.15, 623/1.18, 1.19, 1.2
See application file for complete search history.

(56) References Cited

U.S. PATENT DOCUMENTS

| | | | |
|---|---|---|---|
| 5,064,435 A | 11/1991 | Porter | 623/12 |
| 5,342,300 A * | 8/1994 | Stefanadis et al. | 606/198 |
| 5,383,892 A | 1/1995 | Cardon et al. | 606/198 |
| 5,449,373 A | 9/1995 | Pinchasik et al. | 606/198 |
| 5,466,242 A | 11/1995 | Mori | 606/198 |
| 5,536,274 A | 7/1996 | Neuss | 623/1 |
| 5,540,712 A | 7/1996 | Kleshinski et al. | 606/198 |
| 5,556,413 A | 9/1996 | Lam | 606/198 |
| 5,575,818 A | 11/1996 | Pinchuk | 623/1 |
| 5,617,878 A | 4/1997 | Taheri | 128/898 |
| 5,645,559 A * | 7/1997 | Hachtman et al. | 623/1.2 |
| 5,658,308 A * | 8/1997 | Snyder | 606/198 |
| 5,683,411 A | 11/1997 | Kavteladze et al. | 606/200 |
| 5,716,393 A | 2/1998 | Lindenberg et al. | 623/1 |
| 5,741,333 A | 4/1998 | Frid | 623/12 |
| 5,749,919 A | 5/1998 | Blanc | 623/1 |
| 5,755,769 A | 5/1998 | Richard et al. | 623/11 |
| 5,776,142 A | 7/1998 | Gunderson | 606/108 |
| 5,800,508 A | 9/1998 | Goicoechea et al. | 623/1 |
| 5,800,520 A | 9/1998 | Fogarty et al. | 623/1 |

(Continued)

FOREIGN PATENT DOCUMENTS

EP   0 183 372   10/1985

(Continued)

OTHER PUBLICATIONS

U.S. Appl. No. 09/606,898, filed Jun. 29, 2000, Jon St. Germain.

(Continued)

*Primary Examiner*—Kevin T. Truong
(74) *Attorney, Agent, or Firm*—Vidas, Arrett, Steinkraus

(57) ABSTRACT

A stent having varying outward radial force along its length. In use, the stent can provide greater force in vessel regions requiring greater force and less force in regions requiring less. In particular, more force is provided in the narrowed, center of a stenosis, while not applying too much force to the adjoining healthy tissue area. Greater stent expansion is provided in wider vessel geometries and less stent expansion in narrower regions. Varying force is achieved varying the number of elements, the density of elements, and the thickness of the elements.

12 Claims, 3 Drawing Sheets

U.S. PATENT DOCUMENTS

| | | | |
|---|---|---|---|
| 5,807,404 A | 9/1998 | Richter | 623/1 |
| 5,817,126 A | 10/1998 | Imran | 606/198 |
| 5,824,037 A | 10/1998 | Fogarty et al. | 623/1 |
| 5,827,321 A | 10/1998 | Roubin et al. | 606/195 |
| 5,836,966 A | 11/1998 | St. Germain | |
| 5,843,117 A | 12/1998 | Alt et al. | 606/194 |
| 5,849,037 A | 12/1998 | Frid | 623/1 |
| 5,855,600 A | 1/1999 | Alt | 623/1 |
| 5,868,780 A | 2/1999 | Lashinski et al. | 606/198 |
| 5,868,782 A * | 2/1999 | Frantzen | 606/198 |
| 5,868,783 A | 2/1999 | Tower | 606/198 |
| 5,902,317 A | 5/1999 | Kleshinski et al. | 606/198 |
| 5,913,895 A | 6/1999 | Burpee et al. | 623/1 |
| 5,922,019 A | 7/1999 | Hankh et al. | 623/1 |
| 5,922,021 A | 7/1999 | Jang | 623/1 |
| 5,938,697 A | 8/1999 | Killion et al. | 623/1 |
| 6,146,403 A | 11/2000 | St. Germain | |
| 6,179,867 B1 | 1/2001 | Cox | 623/1.15 |
| 6,273,910 B1 | 8/2001 | Limon | 623/1.15 |
| 6,273,911 B1 | 8/2001 | Cox et al. | 623/1.15 |
| 6,283,992 B1 | 9/2001 | Hankh et al. | 623/1.2 |
| 6,413,272 B1 | 7/2002 | Igaki | 623/1.15 |

FOREIGN PATENT DOCUMENTS

| | | |
|---|---|---|
| EP | 0 183 372 A1 | 6/1986 |
| EP | 0 688 545 A1 | 12/1995 |
| EP | 0 740 928 A2 | 11/1996 |
| WO | 91/16005 | 10/1991 |
| WO | 93/13824 | 7/1993 |
| WO | 93/22986 | 11/1993 |
| WO | 97/25937 | 7/1997 |
| WO | 97/32543 | 9/1997 |
| WO | 98/52497 | 11/1998 |
| WO | 99/01087 | 1/1999 |

OTHER PUBLICATIONS

Product Description, R Stent, The High Tech Revolution, Coronary Stent.

Stent Handbook, An Educational Reference Guide, SciMed Life Systems, Inc., 26 pages, 1996.

* cited by examiner

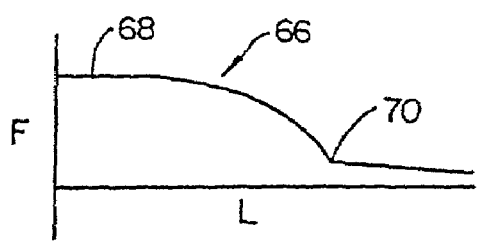
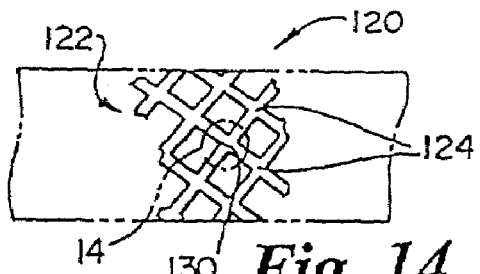
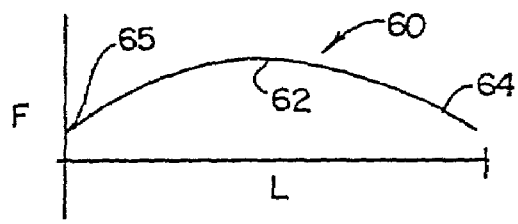
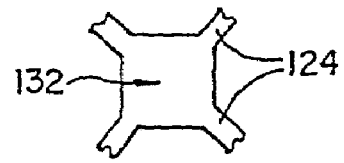
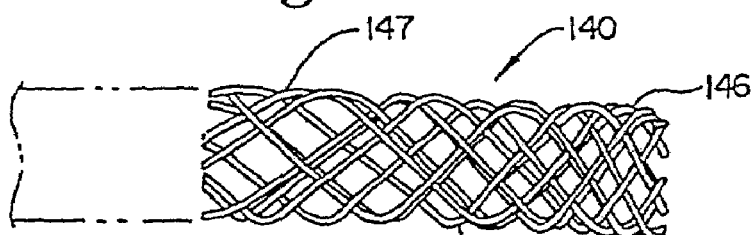
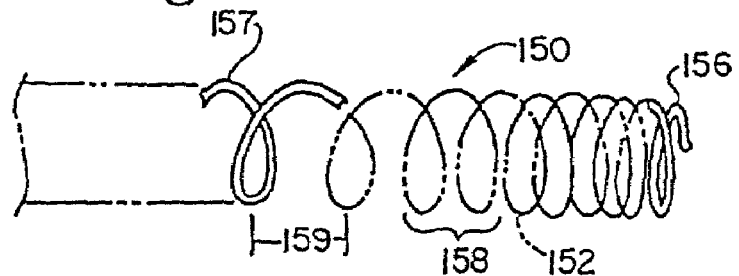

VARIABLE EXPANSION FORCE STENT

CROSS REFERENCE TO RELATED APPLICATIONS

This application is a continuation application from U.S. application Ser. No. 09/606,898 filed Jun. 29, 2000 now U.S. Pat. No. 6,423,084 which is a continuation of U.S. Pat. No. 6,146,403 corresponding to U.S. application Ser. No. 09/193,504, filed Nov. 17, 1998 which is a continuation application from U.S. Pat. No. 5,836,966 corresponding to U.S. application Ser. No. 08/861,798, filed May 22, 1997 the entire contents of each being incorporated herein by reference.

FIELD OF THE INVENTION

The invention relates generally to medical devices. More specifically, the invention relates to stents for holding vessels such as arteries open to flow.

BACKGROUND OF THE INVENTION

Stents are insertable medical devices used to maintain openings for fluid flow in areas that might otherwise close, hindering flow. Stents are used to prevent restenosis after Percutaneous Transluminal Catheter Angioplasty (PTCA), presenting outward radial force against a potentially rebounding vessel wall after balloon widening. Stents are also used to hold open inflamed vessel walls that would otherwise be swollen shut, precluding flow. Stents can also be used to hold open surgically made holes for drainage.

Stents are often tubular devices for insertion into tubular vessel regions. Balloon expandable stents require mounting over a balloon, positioning, and inflation of the balloon to expand the stent radially outward. Self-expanding stents expand into place when unconstrained, without requiring assistance from a balloon. A self-expanding stent is biased so as to expand upon release from the delivery catheter.

A vessel having a stenosis may be modeled as an inwardly protruding arcuate addition of hardened material to a cylindrical vessel wall, where the stenosed region presents a somewhat rigid body attached along, and to, the elastic wall. The stenosis presents resistance to any expansion of the vessel in the region bridged by the stenosis. Stenoses vary in composition, for example, in the degree of calcification, and therefore vary in properties as well.

The arcuate geometry of many stenoses present a variation in resistance along the vessel axis to stent outward radial force. Specifically, stenosed vessel resistance is often greatest toward the middle, lessening toward the ends, with a rapid decrease at the start of healthy vessel tissue.

A conventional self-expanding stent optimally has a length greater than the length of the stenosed region to be kept open. Current stents present a substantially uniform outward radial force along their length. Currently, stents do not vary outward radial force to match stenosis geometries or resistances. A constant force stent, with sufficient force to maintain an open channel within a stenosis, has greater force than necessary in the healthy vessel portion lying past the stenosis ends. The stent ends may thus flare outward, protruding into, and possibly irritating non-stenosed tissue.

Stenosis can occur in vessel regions having asymmetric geometry lying on either side of the stenosis. One example of this is the ostium of a coronary artery, having a wide opening toward the aorta, converging into a narrower coronary artery. A conventional stent placed in the ostium would provide substantially uniform outward force over a non-uniform vessel diameter. If this force is properly matched for the narrower vessel opening, it is likely less than optimal for the wider region.

What would be desirable, and has not heretofore been provided, is a stent capable of providing sufficient force to keep a vessel open within a rebounding stenosis, while providing only necessary force against healthy, non-stenosed vessel regions. What also has not been provided is a stent providing necessary, but only necessary force along a stenosis in a vessel region having non-uniform vessel diameter on either side of the stenosis.

SUMMARY OF THE INVENTION

The present invention includes a self-expanding stent having a tubular shaped structure, where the outward radial force varies with longitudinal position along the length of the stent. In one embodiment, the force is greater in the center and lesser at both ends. Such a stent is suitable for placement in a stenosed vessel region. In another embodiment, the force is less at one end, greater at the middle, and greater still at the opposite end. Such a stent is suitable for placement in a stenosed and narrowing vessel region, including placement near a coronary ostium.

One stent has a structure formed of shape memory material. In one embodiment, the stent is constructed of a Nickel-Titanium alloy.

The stent structure in a preferred embodiment includes a helix formed of a wire having the helix turns spaced more closely together toward the center than at the ends. The helix is biased to expand in outer diameter and contract in length after having been stretched axially and released. In an alternate embodiment, the helix turns increase in spacing from one end to the opposite end. In another embodiment, interwoven or intertwined wires form the tubular structure, with the number of wires being greater per unit length toward the center than at the ends. The interwoven wires can be metallic wire. The wires can resemble spirals or helices after having been wound to the tubular stent shape. In yet another embodiment, the number of wires increase from one end to the opposite end.

One stent achieves a variation in radial force by including in the stent structure elements which intersect at junctions having more material in regions requiring more radial force and less material in regions requiring less radial force. The amount of junction material can be varied by varying the size of the junction area. In a preferred embodiment, the stent structure is formed by laser cutting a Nitinol tube, leaving a greater strut dimension in regions requiring greater outward radial force.

In yet another embodiment, the stent structure includes a series of wire springs having a "zig-zag" shape which each radially encircle a tubular section. The springs are interconnected longitudinally. The required outward radial force can be varied by varying the stent wall thickness in this and other embodiments. In one embodiment, stent regions requiring greater radial force have thicker walls than regions requiring less force.

Stents made in accordance with the present invention can provide an outward radial force more closely matching the local force requirements. In particular, the stents provide greater force only where required in a stenosis center, without providing too much force in the region of healthy tissue. The stents provide an expanded geometry more closely tailored to the requirements of a narrowing vessel region, providing greater expansion in wider regions and less expansion in narrower regions.

BRIEF DESCRIPTION OF THE DRAWINGS

FIG. 5 is a plot of force versus length of an improved stent for placement in FIG. 1;

FIG. 6 is a plot of force versus length of an improved stent for placement in FIG. 4;

FIG. 13 is an enlarged view of element junctions in a self-expanding stent;

FIG. 14 is an enlarged view of an element junction in the self-expanding stent of FIG. 13;

FIG. 15 is an enlarged view of an element junction of a self-expanding stent;

FIG. 16 is a side view of a self-expanding stent having a greater density of elements toward one end; and FIG. 17 is a side view of a self-expanding stent having more closely spaced elements toward one end.

DETAILED DESCRIPTION OF THE PREFERRED EMBODIMENTS

Figure 1:
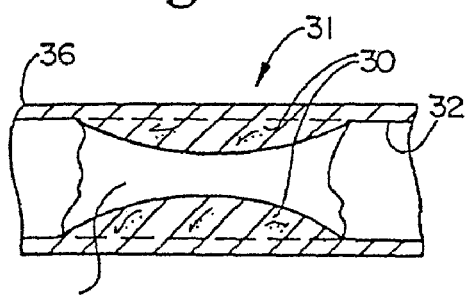
FIG. 1 is a fragmentary longitudinal cross-sectional view of a stenosed vessel region.
Figure 2:
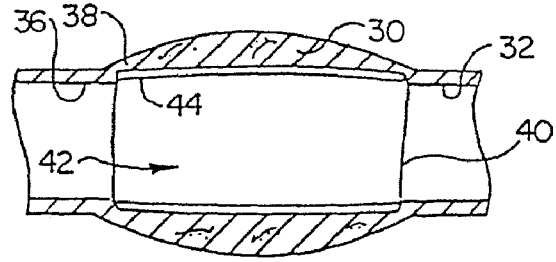
FIG. 2 is a fragmentary cross-sectional view of a stenosed vessel region with a conventional stent in place.
Figure 3:
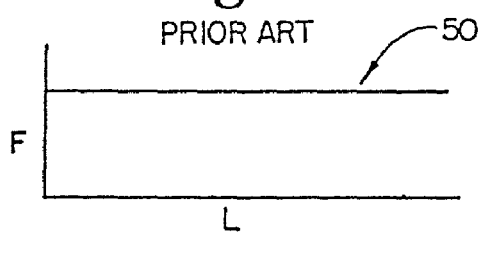
FIG. 3 is a plot of force versus length for the conventional stent of FIG. 2.

FIG. 1 illustrates a stenosis 30, forming narrowed region 34, in a vessel 31 within vessel wall 32. Adjacent to stenosis 30 is a healthy vessel region 36. FIG. 2 illustrates a conventional stent 40 in place across stenosis 30, out of the blood flow channel as indicated at 44. Stent 40 includes a stent end 44, shown angling into healthy vessel area 36 at 38. Stent 40 as shown, has sufficient force to keep vessel 30 open against the rebound force of stenosis 30, and has more force than required at stent end 42, resulting in stent 40 angling into the healthy vessel wall at 38. FIG. 3 illustrates an idealized plot 50 of outward radial force, F, against stent length, L, for a conventional stent such as that illustrated in FIG. 2. As shown, the force is substantially constant over the length.

Figure 4:
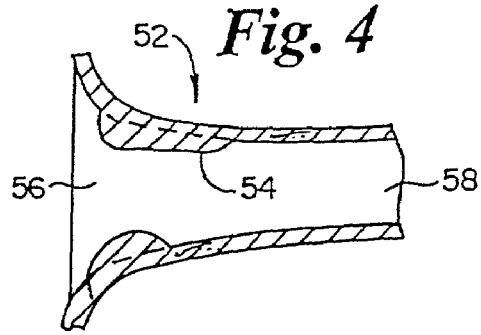
FIG. 4 is a fragmentary longitudinal cross-sectional view of a stenosis in a narrowing vessel region.

FIG. 4 illustrates a narrowing vessel 52 having a wide region 56, a narrowed region 58, and a stenosis 54. The narrowing vessel of FIG. 4 illustrates the geometry as found in an ostium such as the left coronary ostium, where blood from the aorta flows into the left coronary artery. A stent with sufficient force to hold open wide region 56 would have greater force than necessary to hold open narrowed region 58. A stent having the outward radial force axial distribution of FIG. 3, would have insufficient force at wide region 56 and greater than required force at narrowed region 58.

FIG. 5 illustrates a plot 60 of outward radial force F along stent length L for one stent embodying the present invention. The stent has greater force in a middle region 62 than at end regions 64 and 65. A stent having the force curve of FIG. 5 is suitable for bridging a stenosis as illustrated in FIG. 1, while preventing the stent from angling into healthy tissue as show in FIG. 2 at 38. FIG. 6 illustrates a plot 66 of outward radial force F along stent length L for another stent embodying the present invention. The stent has a greater force in end region 68 than at the opposite end region 70. A stent having the force curve of FIG. 6 is suitable for bridging the stenosis as illustrated in FIG. 4, having sufficient force to hold open vessel wide region 56 and less force in vessel narrow region 58, where less is required.

Figure 7:
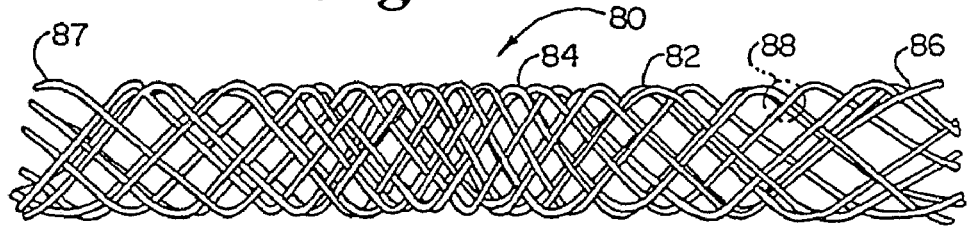
FIG. 7 is a side view of a self expanding stent having more wires per unit length at longitudinal center.

FIG. 7 illustrates a preferred embodiment of the invention producing a force distribution as illustrated in FIG. 5. Self-expanding stent 80 includes numerous resilient wires 82, interwoven as indicated at 88. In use, stent 80 is drawn longitudinally which increases the length and decreases the diameter. Stent 80 is inserted into the distal end of the delivery catheter, advanced to a stenosis to be crossed, and forced out of the delivery catheter distal end. Upon exiting the tube, stent 80 expands radially and shortens axially, pushing against the stenosis and vessel walls.

Stent 80 includes a middle region 84 and end regions 86 and 87. Stent 80 wires 82 are biased to resume the unconstrained state, which is wider and shorter than the constrained stent shape in the tube. The amount of outward radial force exerted per unit length of stent is greater in regions having a greater density of wires per unit length. As illustrated in FIG. 7, stent 80 has a greater number of wires per unit length in center region 84 than in end regions 86 and 87. Thus, stent 80 has a greater outward radial force in center region 84 than in end regions 86 and 87. The greater number of wires per unit length in one embodiment is the result of forming wires, which run the entire stent length, more closely together toward stent center. In another embodiment, the greater number of wires is the result of adding more wires which only run in the center region of the stent.

Figure 8:
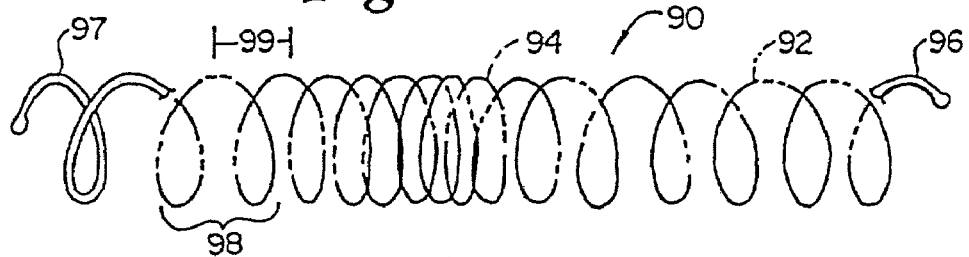
FIG. 8 is a side view of a self-expanding stent coil more-closely spaced toward center.

FIG. 8 illustrates another embodiment of the invention in self-expanding stent 90, having a middle region 94 and end regions 96 and 97. Stent 90 is formed of a single, spirally wound wire 92, forming a helix 98. A preferred embodiment utilizes Nitinol material for wire 92. Helix 98 has a distance between helix turns as indicated at 99. Distance 99 varies with longitudinal position, being greater in middle region 94 and less in end regions 96 and 97. Wire 92 is formed as a spring, biased to resume its unconstrained shape when released, after having been stretched axially. The amount of outward radial force exerted is greater in regions having more wire elements per unit length, which, in stent 90, is achieved by having less space 99 between helix turns. Thus, stent 90 has a greater outward radial force in center region 94 than in end regions 96 and 97.

Figure 9:
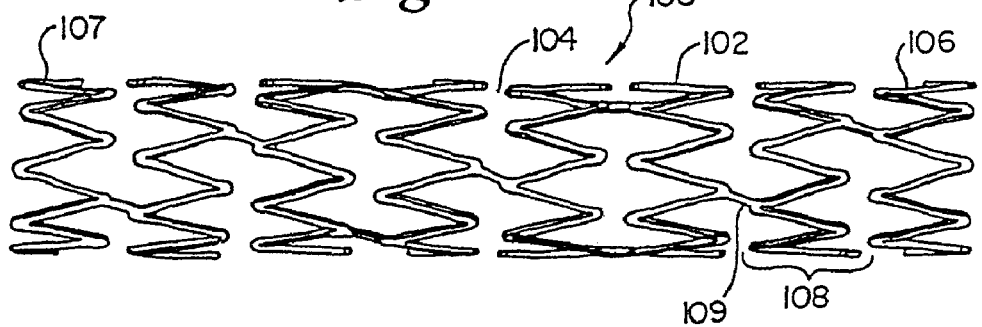
FIG. 9 is a side view of a self-expanding stent having thicker elements toward longitudinal center.
Figure 10:
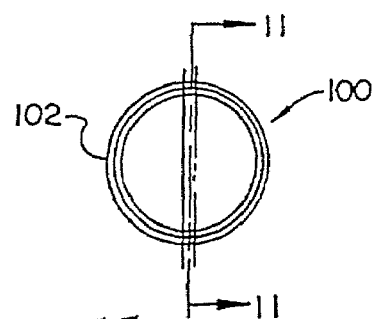
FIG. 10 is an end view of the stent of FIG. 9.

FIG. 9 illustrates still another embodiment of the invention in stent 100, having a middle region 104 and end regions 106 and 107. Stent 100 has a tubular shape formed of a wire 102, which is shaped into several springs 108 having a zig-zag pattern, each spring 108 radially encircling a segment of stent 100, as indicated in FIG. 10. Referring again to FIG. 9, springs 108 are longitudinally interconnected with segments 109. Springs 108 and segments 109 in one embodiment are formed using standard wire bending jigs and techniques, including brazing segments 109 to springs 108. A preferred material for constructing stent 100 is Nitinol. In another embodiment, springs and segments are formed by laser cutting a continuous-walled metallic tube, leaving only springs 108 and segments 109.

Figure 11:
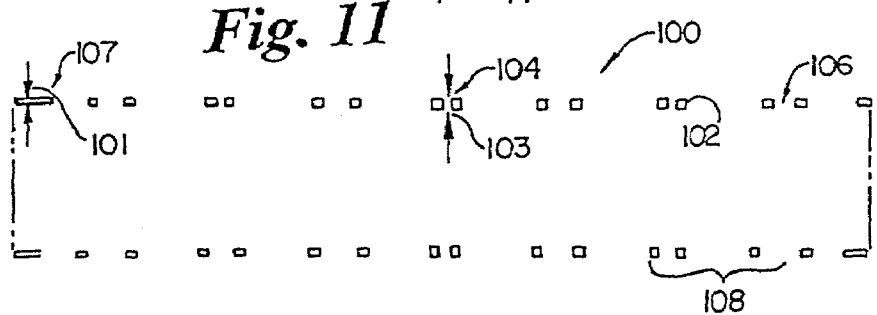
FIG. 11 is a wafer view of the stent of FIG. 9.

FIG. 11 illustrates a wafer section in elevation taken along 11—11 in FIG. 10. Wire elements 102 are illustrated in cross section in middle region 104 and end region 107. The element thickness in width and/or length in end region 107, indicated at 101, is less than the element thickness in middle region 104, indicated at 103. Middle elements having thickness 103 can provide greater outward radial force than end elements having relatively lesser thickness 101. The radial expansive force can also be varied by varying the frequency and/or amplitude of the zig-zag pattern.

Figure 12:
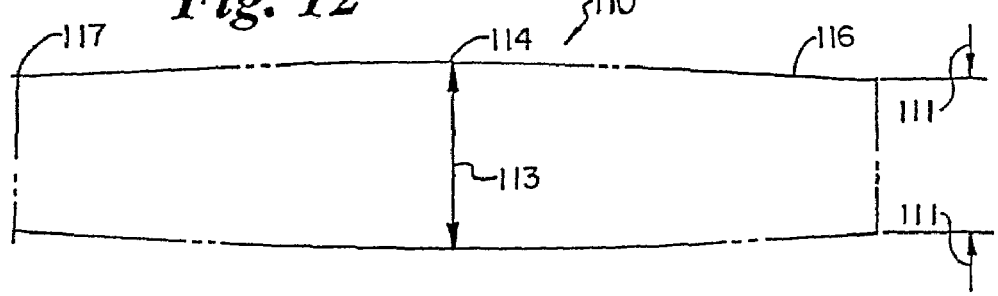
FIG. 12 is a longitudinal profile of an alternate embodiment of the invention in which the diameter is non-uniform along the stent length.

FIG. 12 illustrates, in highly diagrammatic form, a phantom line profile of another embodiment of the invention. A profile of stent 110 is shown in phantom, having a middle region 114 and end regions 116 and 117. Stent 110 is formed, at least in part, from a shape memory material. In the preferred embodiment, stent 110 is formed of Nitinol. Shape memory materials can be annealed into a first shape, heated, thereby setting the material structure, cooled, and deformed into a second shape. The first shape has an average outside diameter greater than the second. The material returns to the first, remembered shape at a phase transition temperature specific to the material composition.

FIG. 12 illustrates the stent shape to be remembered upon reaching body temperature. Stent 110 has a middle outside diameter 113 and end outside diameter 111, where the middle outside diameter is greater than the end outside diameter. Stent 110 can be compressed to fit within the delivery catheter, the delivery catheter advanced to a stenosis, and the stent pushed out the delivery catheter distal end. Stent 110 then begins resuming the remember shape of FIG. 12. The stenosed region typically has the arcuate shape of FIG. 1. As stent middle outside diameter 113 is greater than end outside diameter 111, and the vessel middle inside diameter is typically less than the vessel end inside diameters, stent 110 can provide greater force in applying middle stent region 114 against middle vessel walls than in applying end stent regions 117 and 116 against the end vessel walls.

FIG. 13 illustrates another embodiment of the invention. In particular, FIG. 13 illustrates a tubular stent structure formed of elements meeting at junctions, where the junction size can be varied over the length of the stent. Stent 120 is shown having a structure 122 including elements 124. Elements 124 intersect each other at junction 130 as illustrated in detail in FIG. 14. FIG. 15 illustrates a junction having a greater amount of material than the junction in FIG. 14. In the embodiment of FIG. 15, junction 132 has a greater surface area than junction 130. Junctions having more material have greater capacity to provide radial outward force than junctions having less material. One embodiment of the invention has elements meeting or intersecting at junctions, where the junctions have more material in the tube middle region and less material in the tube end regions. In a preferred embodiment, the junctions are formed by laser cutting a Nitinol tube material.

In use, the tube can be compressed to fit within the delivery catheter, advanced to the stenosis, and pushed distally from the delivery catheter distal end. As the tube regains its uncompressed shape, areas having a greater amount of material at the junctions are able to exert greater outward radial force.

FIG. 16 illustrates an embodiment of the invention suitable for use across stenoses in narrowing vessel regions, such as the left coronary ostium. Stent 140 has a first end region 147 and a second, opposite end region 146. Stent 140 is similar to stent 80 in FIG. 7. The stent tube includes wires 142 which are wound around the stent and can be interwoven. As illustrated in FIG. 16, wires 142 have a greater density per stent unit length at second end region 146 than in first end region 147. This enables second end region 146 to provide greater outward radial force than first end region 147. Thus, first end region 147 can be suitably matched for narrow vessel region 58, with second end region 146 matched for wide vessel region 56.

FIG. 17 illustrates another embodiment of the invention suitable for use across a stenosed, narrowing vessel region. Stent 150 extends from a first end region 157 to a second end region 156. Stent 150 is similar in construction to stent 90 in FIG. 8, including wires 152 formed into a helix or spiral 158. Helix turns are spaced a distance 159 apart. As illustrated in FIG. 17, helix turns are spaced further apart at first end region 157 than at second end region 156. This spacing allows stent 150 to provide greater outward radial force at second end region 156 than at first end region 157.

FIGS. 16 and 17 illustrate two embodiments having greater radial force at one end than the other. This property can be produced using other structures. Another embodiment having this property is similar to a longitudinal half of FIG. 9, having a greater element thickness at one end than the other. Yet another embodiment is similar to a longitudinal half of FIG. 12, having a greater outside diameter at one end than the other.

Stents providing greater outward radial force at one end than another, as in the embodiments of FIGS. 16 and 17, allow a stent to be placed across a stenosis in a narrowing vessel region as illustrated in FIG. 4. The stent end having a greater radial force can expand into the wider vessel region, while the stent end having lesser radial force can expand to the narrower vessel region wall, but with less force than if required to expand as far as the stent end in the wider vessel region. This can lessen unneeded force on the vessel wall while still holding the vessel open and keeping the stent substantially out of the vessel flow path.

The present invention provides a stent having a radial force varied along stent length. The stent has been described, in use, as bridging stenosed vessel regions for illustrative purposes. Another use is maintaining open channels through inflamed or otherwise restricted body conduits. Stents used for other purposes are explicitly within the scope of the invention.

It should be noted that although self-expanding stents have been shown herein to illustrate the present invention, so called balloon expandable stents can also include the variable expansion force feature as described herein. In the case of balloon expandable stents, however, these forces in general will be less than are necessary to expand the stent and thus the balloon will be used as known to those skilled in the art to complete the expansion of the stent. These balloon expandable stents may be advantageously deployed in bending areas of a vessels such as at an ostium where a stent having thus rigid or heavy members is desirable to enhance the flexibility of the stent. It should be understood therefore, that balloon expandable stents are also within the scope of the present invention.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A self-expanding stent the stunt having a length, the stent expandable from an unexpanded state to an expanded state, the radius of the stent in the unexpanded state constant along the length of the stent, the stent comprising:
   a tubular shaped structure made of a plurality of interwoven wires of shape memory material, said structure having a radially outward biased force, said force being varied along said length, said tubular structure defining a plurality of regions along the length, one of the regions having a greater density of wires than the other regions, the at least one region having a greater radially outward biased force than the other regions.

2. The stent of claim 1 wherein the plurality of regions comprise a middle region positioned between a first end region and a second end region.

3. The stent of claim 2 wherein the middle region has the greater density of wires.

4. The stent of claim 3 wherein the middle region has the greater radially outward biased force.

5. The stent of claim 2 wherein at least one of the first end region and second end region has the greater density of wires.

6. The stent of claim 5 wherein at least one of the first end region and second end region has the greater radially outward biased force.

7. The stent of claim 2 wherein at least one of the plurality of interwoven wires is helically wound.

8. The stent of claim 7 wherein the helically wound wire includes a plurality of turns, the turns having an axial spacing, the axial spacing being greater in the first end region than in the middle region and greater in the second earl region than in the middle region.

9. The stent of claim 7 wherein the plurality of interwoven wires are helically wound.

10. The stent of claim 2 wherein the number of wires increases from the first end region to the middle region and from the second end region to the middle region.

11. The stent of claim 2 wherein the amount of shape memory material increases from the first end region to the middle region and from the second end region to the middle region.

12. The stent of claim 1 formed of Nitinol.

* * * * *